United States Patent

Rangert et al.

[11] Patent Number: 5,772,437
[45] Date of Patent: Jun. 30, 1998

[54] SECURING ELEMENT

[75] Inventors: Bo Rangert, Mölnlycke, Sweden; Burton Langer, New York, N.Y.; Ulf Johansson, Onsala, Sweden

[73] Assignee: Nobel Biocare AB, Gothenburg, Sweden

[21] Appl. No.: 507,257
[22] PCT Filed: Dec. 20, 1994
[86] PCT No.: PCT/SE94/01226
  § 371 Date: Oct. 5, 1995
  § 102(e) Date: Oct. 5, 1995
[87] PCT Pub. No.: WO95/17135
  PCT Pub. Date: Jun. 29, 1995

(Under 37 CFR 1.47)

[30] Foreign Application Priority Data

Dec. 20, 1994 [SE] Sweden .................................. 9304208

[51] Int. Cl.[6] .................................................. A61C 8/00
[52] U.S. Cl. .............................................................. 433/174
[58] Field of Search ..................... 433/172, 173, 433/174, 175, 176

[56] References Cited

U.S. PATENT DOCUMENTS

D. 296,362  6/1988  Branemark .
4,330,891  5/1982  Branemark et al. ............................. 3/1
4,790,753  12/1988  Fradera .................................... 433/174
4,842,518  6/1989  Linkow et al. ........................... 433/174
4,960,381  10/1990  Niznick .................................... 433/174
4,976,739  12/1990  Duthie, Jr. ........................... 433/174 X
5,030,095  7/1991  Niznick .............................. 433/174 X
5,269,685  12/1993  Jorneus et al. .......................... 433/174
5,312,256  5/1994  Scortecci ................................. 433/174
5,338,197  8/1994  Kwan ..................................... 433/174

FOREIGN PATENT DOCUMENTS 4096745  3/1992  Japan ..................................... 433/174
 38454  of 1986  Sweden .

Primary Examiner—Nicholas D. Lucchesi
Attorney, Agent, or Firm—Pollock, Vande Sande & Priddy

[57] ABSTRACT

The invention relates to a screw-type securing element, made of titanium, for permanent anchoring in bone tissue, in particular for permanent anchoring of artificial teeth and dental bridges in the jaw bone, the securing element having an outer threaded portion which at the far top merges into a smooth, conical and/or cylindrical flange (5, 9). The thread end is such that the thread (1) in the periosteal part of the securing element merges into the flange (5, 9) via a cylindrical groove (7) which has the geometry of the threading die. By means of maintaining, in this way, a correct thread pitch and thread depth right up to the flange, a geometrically satisfactory match is obtained, in which the previously threaded hole matches the geometry of the thread right up to the flange, which means that the cortical bone can be better utilized.

6 Claims, 2 Drawing Sheets

SECURING ELEMENT

FIELD OF THE INVENTION

The present invention relates to a screw-type securing element, made of titanium, for permanent anchoring in bone tissue, in particular for permanent anchoring of artificial teeth and dental bridges in the jawbone. The securing element has an outer threaded portion which at its far top merges into a smooth conical and/or cylindrical portion. The front part of the screw is preferably provided with one or more recesses whose margins adjoining the circular symmetrical surface of the securing element form cutting edges permitting self-tapping when the element is being screwed into the bone tissue.

BACKGROUND OF THE INVENTION

Screw-type securing elements, made of titanium, for replacing lost teeth have been shown to have many advantages. The outer thread of the securing element provides a natural positive locking in the bone and gives initial stability, and also distributes the load favorably to the surrounding bone tissue. Recent long-term clinical follow-up studies have underlined the fact that threaded securing elements are in this respect more advantageous than the unthreaded ones. The position of the boundary area where the thread merges into a smooth, cylindrical or conical surface is for this reason of great importance with regard to the function of the securing element, i.e. the implant. This position usually determines where, on the securing element, long-term stabilizing of the bone tissue occurs.

To obtain initial stabilizing of the securing element, and to place the latter in a predetermined position, it is already known to have the thread end with a flange. The flange means that there is a possibility of mechanical resistance with increased initial stability and results in more reliable positioning. The initial stability is considered to be important for ensuring incorporation, and the improved positioning in the axial direction affords greater protection against penetration into the nerve channel of the mandible.

The flange also makes it possible for the soft tissue to seal off the oral cavity directly against the fixture, and any bacterial leakage through the spacer piece does not reach the bone level. The flange can thus be regarded as a first part of the spacer system attached to the fixture (or a first part of the implant part penetrating the soft tissue).

However, when the thread is being chased, the flange represents an obstacle to the runout of the thread cutter, for which reason a turned recess is usually formed under the flange to lift the cutter out without damaging the flange. However, this means that approximately one thread turn is lost on the securing element, which leads to the marginal bone height lying correspondingly further down on the securing element. This loss is critical in some cases, since it means that it is not possible to use the outermost bone edge, which normally has the best mechanical properties. It is also important, particularly in the case of thin bone, that the thread be fully used to obtain good initial stability of the implanted securing element.

An alternative production procedure is to allow the thread cutter to be drawn out only radially, but this results in an increasingly shallower thread, which does not fit in the already threaded hole, and an undefined flange is obtained. Thus, this method also does not solve the problem of how to fully use the outermost bone edge.

The loss of marginal bone height is especially critical in the use of a small number of implants in the molar areas of the jaw, since an unfavorable loading can occur in this region, especially in the case of an individual molar. A considerable increase in the strength of the implant can, of course, be obtained simply by increasing the dimensions of the implant, but it is far from certain that the existing bone volume will permit this. Omitting the flange, and allowing the thread to run right to the top, is not an optimal solution either, considering the advantages which a flange affords, namely being a counterstay for the initial tightening, and an active, sealing part of the area of the implant passing through the soft tissue.

The hardness of the bone in the molar areas of the jaw can vary greatly. In some patients, only a very thin outer layer, the cortical bone, is hard, while the remaining inner bone, the so-called spongiosa, is very soft. In these bone types, it is already known to use self-tapping fixtures, see for example SE 468,154.

The advantage of self-tapping fixtures is that the implantation of the fixture in the jaw bone is simplified. The normal procedure in fact involves drilling a hole in the bone. In this connection, drills of increasing diameter are successively used until the diameter of the hole corresponds with the core diameter of the threaded fixture. A threading tap is then used, to form the thread in which the implant is placed. When using a self-tapping fixture of the type which is described in the abovementioned patent, the implantation is performed without using a thread tap. However, the use of self-tapping fixtures does not, in itself, solve the problem of loss of marginal bone height.

SUMMARY OF THE INVENTION

The object of this invention is to provide an implant which is based on a presently known basic design and dimensions, but in which the boundary area where the thread merges into the smooth, cylindrical or conical portion, i.e. the thread end, has been given a novel configuration, with the intention of having the marginal bone height lie higher up on the implant so that the cortical bone is better utilized. This is achieved by the fact that the thread in the periosteal part of the implant merges into (i.e. ends at) the smooth, cylindrical or conical portion via a cylindrical groove which has the geometry of the threading die.

In a first embodiment, the smooth portion, against which the thread ends, is formed by a cylindrical flange. As has been pointed out in the introduction, the flange constitutes a counterstay for the initial tightening of the implant and permits positioning of the implant at a precisely determined height. By having the thread now end against the flange via a cylindrical groove which has the profile of the thread, no thread turn is lost on the implant. Consequently the cortical bone can be utilized right up to the flange.

In a second embodiment, the smooth portion against which the thread ends, is formed by a conical portion. In this case too, the thread ends against the conical portion via a cylindrical groove which has the profile of the thread, in direct connection with the conical portion, and the cortical bone can be utilized right up to the conical portion. The conical portion in some cases provides the additional advantage, as compared with a cylindrical flange, that precise preparation of the position of the conical implant flange is made possible by using a conical countersink. This will be described in greater detail below.

The invention will be described in greater detail below with reference to the attached drawing, in which.

DESCRIPTION OF THE PREFERRED EMBODIMENT(S)

Figure 1:
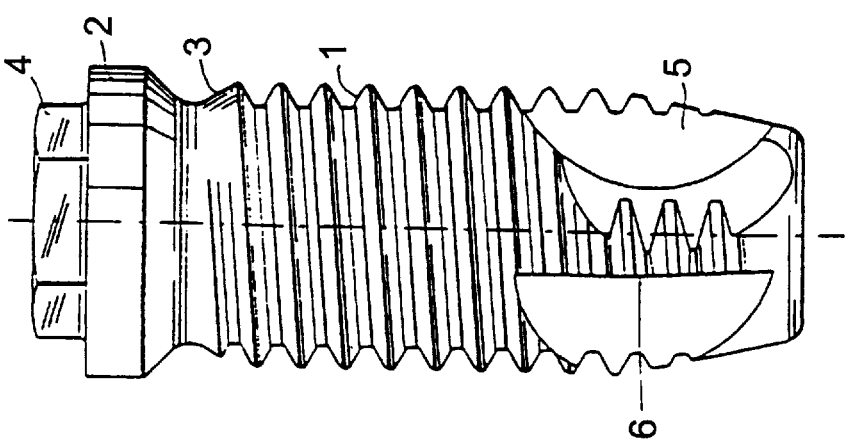
FIG. 1 shows a previously known implant (prior art)

FIG. 1 shows a self-tapping fixture according to the BRANEMARK SYSTEM which is marketed by Nobel Biocare AB. The fixture consists of an essentially cylindrical screw with an outer thread 1, which merges into a wider cylindrical flange 2 via an unthreaded transition portion 3 with a so-called "shallowing-out" thread. The screw is intended to be introduced into a hole already drilled in the jaw bone for permanent anchoring of artificial teeth and dental bridges. The screw has an upper hexagonal portion 4 intended to cooperate with a tool for implanting the screw. The screw is preferably made of commercially pure titanium with a surface structure in accordance with SE-PS 79.02035-0. The screw is self-tapping by virtue of its lower part being provided with three recesses 5 formed in the circular symmetrical surface of the screw. The recesses are designed to form, in connection with the circular symmetrical surface, cutting edges 6, and together they have such a volume that the bone slivers cut off by the cutting edges are accommodated within the recesses; see also above-mentioned SE-PS 91.02451-3.

As mentioned in the introduction, there are certain applications where this fixture does not give the best results, namely in the molar areas of the jaw where there is a relatively thin, hard cortical bone and an inner, porous soft bone. When the screw is implanted in this region, the relatively elongate transition portion 3 with the shallowing-out thread comes to lie opposite the hard cortical bone, and thus the advantages of the thread, with regard to positive locking and stability, are not exploited to the fullest extent.

Figure 2:
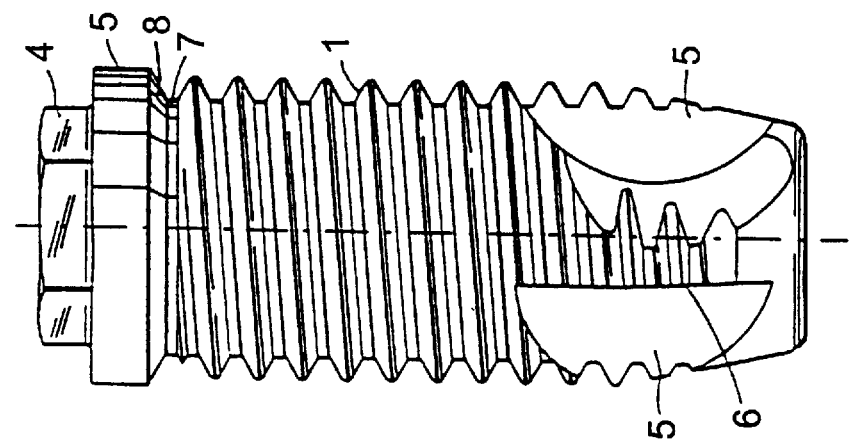
FIG. 2 shows a first illustrative embodiment of an implant according to the invention, with a cylindrical flange.
Figure 3:
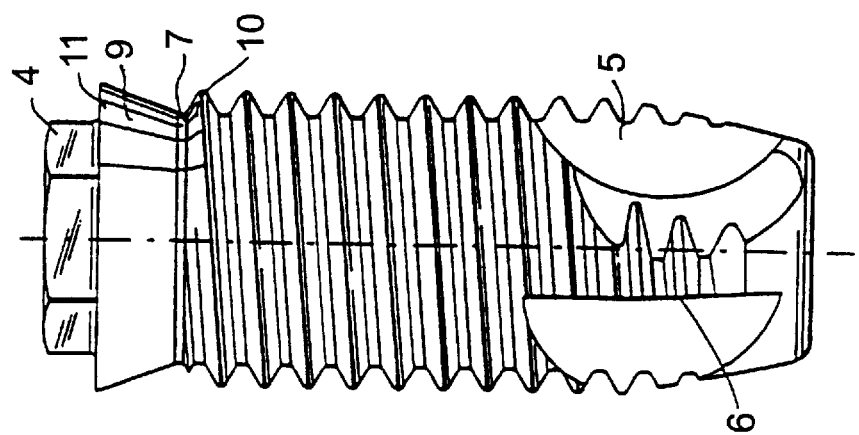
FIG. 3 shows a second embodiment according to the invention, in which the flange is conical.

FIGS. 2 and 3 show how it is possible according to the present invention to minimize transition portion 3 by allowing the thread to end against the flange via a cylindrical groove 7 which has the profile of the thread at the point of connection to the flange. In this way, no thread turn is lost on the fixture, so that the cortical bone can be fully utilized right up to the flange.

The thread end is produced in principle in two stages. When the thread cutter reaches the flange during production, the cutter is drawn radially outwards at an angle which, with respect to the axis of the screw, is at least as great as the angle of the thread flank. In this way, a correct thread pitch is obtained right up to the flange, and the thread merges into the flange with a shallowing-out portion. In the second stage in the production of the thread end, that part of the flange which adjoins the thread is then chased with a profile which corresponds to the profile of the thread. In this way, the thread merges into a groove 7 having the profile of the thread, which groove constitutes the connection of the flange to the thread, with gradually decreased thread width and height, but with the thread depth being maintained. The thread runs right up to the flange, and at the same time the flange remains completely intact, and the shallowing-out thread has been eliminated. This also means that no part of the hole already threaded in the bone is destroyed when the securing element is implanted. With the previously known, shallowing-out thread, there was a possible risk of asymmetrical clamping effects, which can thus be avoided with the novel thread end.

One effect of the cylindrical groove under the flange is that there is no full contact between the flange and the uppermost thread turn in the bone. However, this disadvantage is considered small compared to the disadvantage of having a thread which presses the bone asymmetrically under the flange.

The cylindrical flange 5 in FIG. 2 otherwise corresponds entirely to the flange on the previously known fixture, which is shown in FIG. 1. The pitch and cross-section of the thread are also the same as present day standards. Because a correct thread pitch and thread depth are maintained right up to the flange, the profile angle of the flank 8, which is that part of the groove 7 adjoining the flange 5, approaches in size the flank angle of the thread, which in this case is 60°.

In FIG. 3, the invention is illustrated with respect to a conical flange 9. In this case too, the thread adjoins the conical portion 9 via a cylindrical groove 7, the flank 10 of the groove against the thread having the same profile angle as the flank angle of the thread, while the "flank" of the groove against the flange 9 in this case consists of the flange itself.

Fixtures with conical flanges are already known; see, for example, Swedish design registration 38.454. What is new in this case is the thread ending against the conical flange in the form of the cylindrical groove 7. In addition, the conical flange has the same height as the cylindrical flange, i.e. a comparatively short flange in relation to the conical flange which is shown in the aforementioned design. In the present case, the flange has a height of 1.1 mm, its diameter at the thread connection is the same as the core diameter of the thread, i.e. 4.9 mm, and its diameter at the upper plane 11 is 5.2 mm. The diameter of the fixture, the outer thread, is nominally 5.0 mm.

The reason why it is desirable, in certain applications, to work with a conical flange is that the latter, in conjunction with a conical countersink, permits a more exact anchoring of the implant. By providing the already drilled hole with conical countersinking, which corresponds to the conical flange, a more exact adaptation between the cortical bone and the implant is obtained. The flange also helps in this way, together with the thread, to provide the desired initial stability, which is especially important in the comparatively thin cortical bone.

Upon application in areas with thin cortical bone and a soft trabecular core, it is sometimes desirable to completely eliminate the countersinking completely. Even in such a situation, the conical spacer is considered to be advantageous since it provides a gradually increasing resistance, which gives better protection against the flange losing its hold than is possible with a cylindrical flange. In this type of bone, it is often desired to place the fixture in a previously drilled seat of under-dimensioned diameter in the trabecular bone, when it is desired to widen the entrance in the cortical bone. The conical countersink here makes it possible to widen the cortical bone carefully in this area. The conical countersink can be used for holes measuring from 3 mm upwards. An advantage of the conical flange geometry is that the same countersink can be used for different fixture diameters. The surgeon can choose which degree of clamping effect is desired upon fitting each fixture, since the conical flange presses the bone out essentially radially. As long as the flange is not drawn under the bone edge, the stability will be maintained.

The conical countersink can also be used for widening the cortical entrance, instead of using a twist drill. The advantage of this is that, in such a reaming operation, the bone is worked radially, i.e. essentially in the plane of the bone, which means that it is possible to shape the hole to the desired diameter with considerably less risk of fracture of the cortical plate. When a twist drill is used, the work is performed essentially axially, which involves pressing on the bone shell. In addition, the twist drill has a tendency to cut a groove-shaped hole in thin plates, in which case there is a risk of fragmentation.

The thread end for the conical spacer is also produced in principle in two stages as discussed above.

Figure 4:
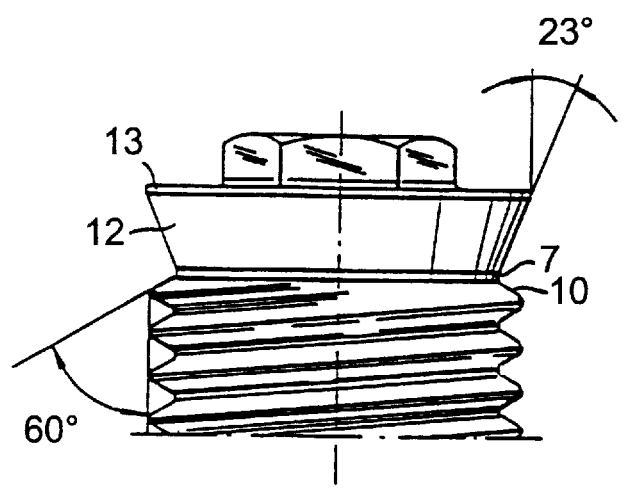
FIG. 4 shows an example in which the flange is made up of a combination of a conical and a cylindrical surface.
Figure 5A:
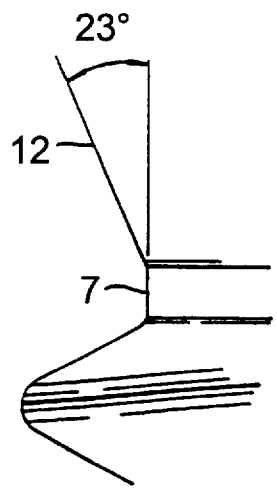
FIG. 5 shows an enlarged view of the thread end.

In FIG. 4, the invention is illustrated with respect to a flange which has a lower conical part 12 and an upper, narrower cylindrical part 13. In this case too, the cylindrical groove 7 has a flank 10 against the thread, the flank having the same flank angle as the flank angle of the thread, i.e. 60°. The cylindrical groove 7 merges directly into the conical flange 12, which in this case has a cone angle of 23°. This is shown on an enlarged scale in FIG. 5a.

Figure 5B:
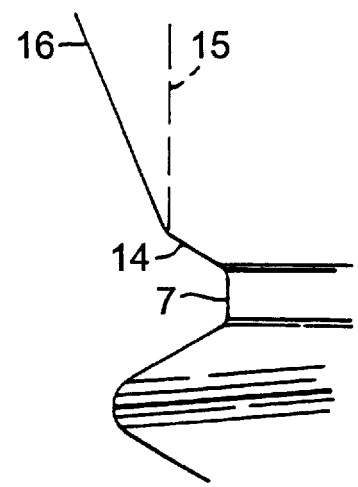

FIG. 5b shows an enlarged view of the case in which the flank 14, of the cylindrical groove 7 which adjoining the flange also has the geometry of the threading die, i.e. a flank angle of 60°. The case with a cylindrical flange 15 and the case with a conical flange 16 have both been indicated in the figure.

The invention is not limited to the embodiments shown by way of example, but instead can be varied within the scope of the patent claims attached.

We claim:

1. A screw-type securing element, made of titanium, for permanent anchoring in bone tissue, the securing element having:
   a lower, threaded outer portion and an upper smooth outer portion, said threaded outer portion merging into said smooth outer portion via a cylindrical groove, said cylindrical groove having a profile corresponding to that of the threads of the threaded portion at a point of connection to the smooth outer portion substantially along the periphery of the securing element.

2. A securing element according to claim 1 wherein the smooth outer portion, against which the threaded portion ends, is formed by a cylindrical flange, and wherein a part of said cylindrical groove adjoining the cylindrical flange comprises a flank whose profile angle is of the same size as the flank angle of the threads.

3. A securing element according to claim 1 wherein the smooth outer portion, against which the threaded portion ends, is formed as a conical flange, and wherein the flank of the cylindrical groove adjoining the threads of the threaded portion has the same profile angle as the flank angle of the threads, and wherein the flank of the cylindrical groove against the conical flange comprises at least partly the conical surface.

4. A securing element according to claim 3 wherein the diameter of said conical flange at said point of connection is equal in size to the core diameter of the threads, and the diameter at the upper plane of said conical flange slightly exceeds the outer diameter of the threads.

5. A securing element according to claim 1 further including a forward part provided with at least one recess whose margin adjoining a circular symmetrical surface of the securing element forms cutting edges in order to permit self-tapping when the element is being screwed into the bone tissue.

6. A method for producing a securing element for anchoring in bone tissue and including a lower, threaded outer portion and an upper smooth outer portion forming a flange, the threaded outer portion merging into said smooth outer portion via a cylindrical groove, the cylindrical groove having the profile corresponding to that of the threads of the threaded portion at a point of connection to the smooth outer portion, said method including the steps of:
   reaching said flange with a thread cutter;
   drawing the cutter straight out at an angle which, with respect to the longitudinal axis of the securing element, is at least as great as the angle of the threads flank; and
   chasing the part of the flange adjoining the threads with the profile of the threads and providing said cylindrical groove with a profile corresponding to that of the threads of the threaded portion at a point of connection to the smooth outer portion substantially along the periphery of the securing element.

* * * * *

UNITED STATES PATENT AND TRADEMARK OFFICE
CERTIFICATE OF CORRECTION

PATENT NO. : 5,772,437
DATED : June 30, 1998
INVENTOR(S): RANGERT et al.

It is certified that error appears in the above-identified patent and that said Letters Patent is hereby corrected as shown below:

On the title page,
  item, [30], change "Dec. 20, 1994" to --Dec. 20, 1993--.

Signed and Sealed this

Twenty-fifth Day of August, 1998

Attest:

BRUCE LEHMAN

*Attesting Officer*  *Commissioner of Patents and Trademarks*